(12) United States Patent
Shapirov

(10) Patent No.: US 8,492,721 B2
(45) Date of Patent: Jul. 23, 2013

(54) SYSTEMS AND METHODS FOR NEAR INFRA-RED OPTICAL INSPECTION

(75) Inventor: Diana Shapirov, Yokneam (IL)

(73) Assignee: Camtek Ltd., Migdal Haemek, IL (US)

( * ) Notice: Subject to any disclaimer, the term of this patent is extended or adjusted under 35 U.S.C. 154(b) by 300 days.

(21) Appl. No.: 12/898,734

(22) Filed: Oct. 6, 2010

(65) Prior Publication Data

US 2011/0102771 A1 May 5, 2011

Related U.S. Application Data

(60) Provisional application No. 61/251,936, filed on Oct. 15, 2009.

(51) Int. Cl.
*G01N 21/00* (2006.01)
(52) U.S. Cl.
USPC .................................. 250/339.05; 356/237.1
(58) Field of Classification Search
USPC .............. 250/338.1, 339.01, 339.05, 339.09, 250/339.12; 356/73, 237.1, 237.5
See application file for complete search history.

(56) References Cited

U.S. PATENT DOCUMENTS

| 7,019,296 | B2 * | 3/2006 | Treado et al. | 250/339.07 |
| 2003/0202180 | A1 * | 10/2003 | Gobel et al. | 356/326 |
| 2004/0211894 | A1 * | 10/2004 | Hother et al. | 250/269.1 |
| 2006/0033026 | A1 * | 2/2006 | Treado et al. | 250/339.07 |
| 2009/0321646 | A1 * | 12/2009 | Cozzolino | 250/339.05 |

* cited by examiner

*Primary Examiner* — Mark R Gaworecki
(74) *Attorney, Agent, or Firm* — Oren Reches

(57) ABSTRACT

An inspection system and a method for defect detection, the method includes: generating a first beam that comprises a near infrared spectral component and a visible light component; directing at least the near infrared spectral component of the first beam towards an inspected object; directing, towards a sensor, a near infrared spectral component of a second beam generated from the illuminating of the inspected object; wherein the sensor is sensitive to visual light radiation and to near infrared radiation; generating, by the sensor, detection signals that are responsive to the near infrared component of the second beam; and detecting defects in the inspected object by processing the detection signals.

18 Claims, 17 Drawing Sheets

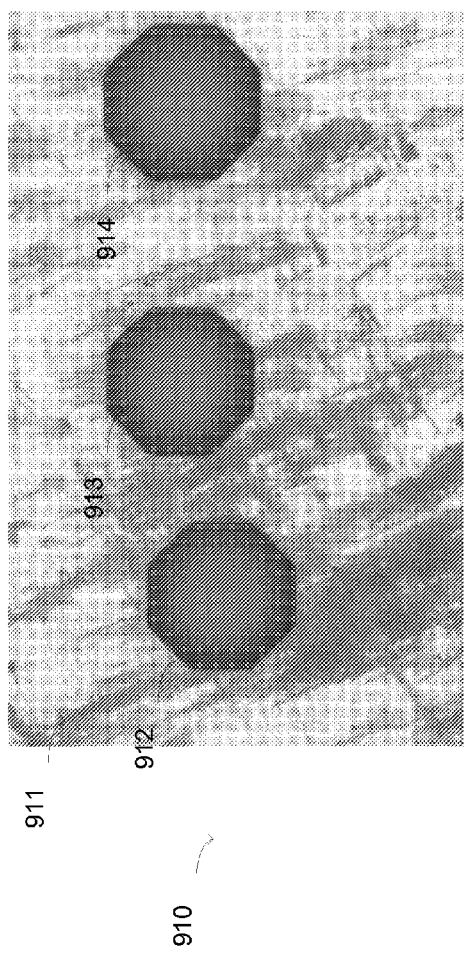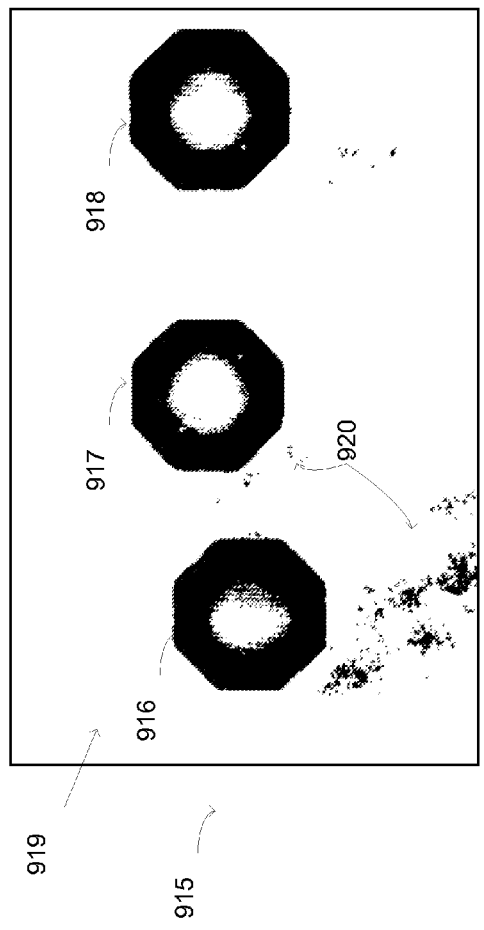
FIG. 11

SYSTEMS AND METHODS FOR NEAR INFRA-RED OPTICAL INSPECTION

RELATED APPLICATIONS

This application claims priority from U.S. patent provisional patent Ser. No. 61/251,936, filing date Oct. 15, 2009.

BACKGROUND OF THE INVENTION

Printer Circuit Boards (PCBs) include Copper conductors. Copper conductors may get oxidized. While copper oxidation does not cause PCB failures, the color change associated with the oxidation often causes many false alarms (false positives) during optical inspection.

Cupric Oxide, Cuprous Oxide, Copper Chloride and Copper Carbonate tend to absorb light and to be imaged as dark pixels that once compares to Copper cause false positives. Similar effects may occur in other oxidized metals in inspected objects.

Other chemical reactions may also result in color change, while not severely reducing the performance of the chemically reacted object (e.g. the copper conductors).

There is a growing need to provide robust optical inspection systems and methods that are less sensitive to Copper oxidation.

SUMMARY

According to an embodiment of the invention a method for defect detection is provided. The method may include generating a first beam that comprises a near infrared spectral component and a visible light component; directing at least the near infrared spectral component of the first beam towards an inspected object; directing, towards a sensor, a near infrared spectral component of a second beam generated from the illuminating of the inspected object; wherein the sensor is sensitive to visual light radiation and to near infrared radiation; generating, by the sensor, detection signals that are responsive to the near infrared component of the second beam; and detecting defects in the inspected object by processing the detection signals.

The method may include substantially preventing radiation outside a near infrared band from reaching the sensor.

The near infrared spectral component of the first beam may be weaker than the at least one visible light component of the first light beam.

The inspected object may include silicon and metal structures, and wherein sensor may be located to sense a near infrared spectral component of the second beam that passes through the inspected object.

The method may include directing at least the near infrared spectral component of the first beam towards metal elements of the inspected object; and generating, by the sensor, detection signals that are substantially indifferent to different levels of oxidation of the metal elements of the inspected object.

The sensor may be a visible light sensor that is also arranged to sense near infra red radiation.

The method may include substantially preventing radiation outside a near infrared band from reaching the sensor and generating, by the sensor, detection signals that are responsive to the near infrared component of the second beam, when an inspection system that comprises the sensor operates in a near infra red mode; and substantially preventing radiation outside a visible light band from reaching the sensor and generating, by the sensor, detection signals that are responsive to a visible light component of the second beam, when the inspection system operates in a visual light mode.

The near infrared band may range between a wavelength of about 700 nanometers and a wavelength of about 1100 nanometers.

The illuminating may include directing the first beam at an angle that is oriented in relation to an imaginary normal to the inspected object by at least twenty degrees.

The illuminating may include directing the first beam at an angle that is oriented in relation to an imaginary normal to the inspected object by about sixty degrees.

According to an embodiment of the invention an inspection system is provided. The inspection system may include an illumination source arranged to generate a first beam that comprises a near infrared spectral component and a visible light component; optics arranged to: direct at least the near infrared spectral component of the first beam towards an inspected object; direct, towards a sensor, a near infrared spectral component of a second beam generated from the illuminating of the inspected object; wherein the sensor is sensitive to visual light radiation and to near infrared radiation; wherein the sensor is arranged to detect signals that are responsive to the near infrared component of the second beam; and a processing circuit arranged to detect defects in the inspected object by processing the detection signals.

The system may include a filter for substantially preventing radiation outside a near infrared band from reaching the sensor.

The near infrared spectral component of the first beam may be weaker than the at least one visible light component of the first light beam.

The inspected object may include silicon and metal structures, and wherein the sensor may be located to sense a near infrared spectral component of the second beam that passes through the inspected object.

The optics may be arranged to direct at least the near infrared spectral component of the first beam towards metal elements of the inspected object; and wherein the sensor may be arranged to generate detection signals that are substantially indifferent to different levels of oxidation of the metal elements of the inspected object.

The sensor may be a visible light sensor that is also arranged to sense near infra red radiation.

The filter may be arranged to substantially prevent radiation outside a near infrared band from reaching the sensor and the sensor is arranged to generate detection signals that are responsive to the near infrared component of the second beam, when the inspection system operates in a near infra red mode; and the filter may be further arranged to substantially prevent radiation outside a visible light band from reaching the sensor and the sensor is further arranged to generate detection signals that are responsive to a visible light component of the second beam, when the inspection system operates in a visual light mode.

The near infrared band may range between a wavelength of about 700 nanometers and a wavelength of about 1100 nanometers.

The optics may be arranged to direct the first beam at an angle that is oriented in relation to an imaginary normal to the inspected object by at least twenty degrees.

The optics may be arranged to direct the first beam at an angle that is oriented in relation to an imaginary normal to the inspected object by about sixty degrees.

According to an embodiment of the invention a method for defect detection is provided. The method may include generating a first beam that comprises a near infrared spectral component; directing the near infrared spectral component of the first beam towards metal elements of an inspected object; directing, towards a sensor, a near infrared spectral component of a second beam generated from the illuminating of the inspected object; wherein the sensor is sensitive to near infrared radiation; generating, by the sensor, detection signals that are substantially indifferent to different levels of oxidation of the metal elements of the inspected object; and detecting defects in the inspected object by processing the detection signals.

The method may include substantially preventing radiation outside a near infrared band from reaching the sensor.

According to an embodiment of the invention a method for defect detection is provided. The method may include generating a first beam that comprises a near infrared spectral component; directing the near infrared spectral component of the first beam towards metal elements of an inspected object; directing, towards a sensor, a near infrared spectral component of a second beam that passed through the inspected object; wherein the sensor is sensitive to near infrared radiation; generating, by the sensor, detection signals; and detecting defects in the inspected object by processing the detection signals.

BRIEF DESCRIPTION OF THE PRESENT INVENTION

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIGS. 10 and 11 illustrate images of an area of an inspected object and binary images of the area, according to an embodiment of the invention;

Figure 12:
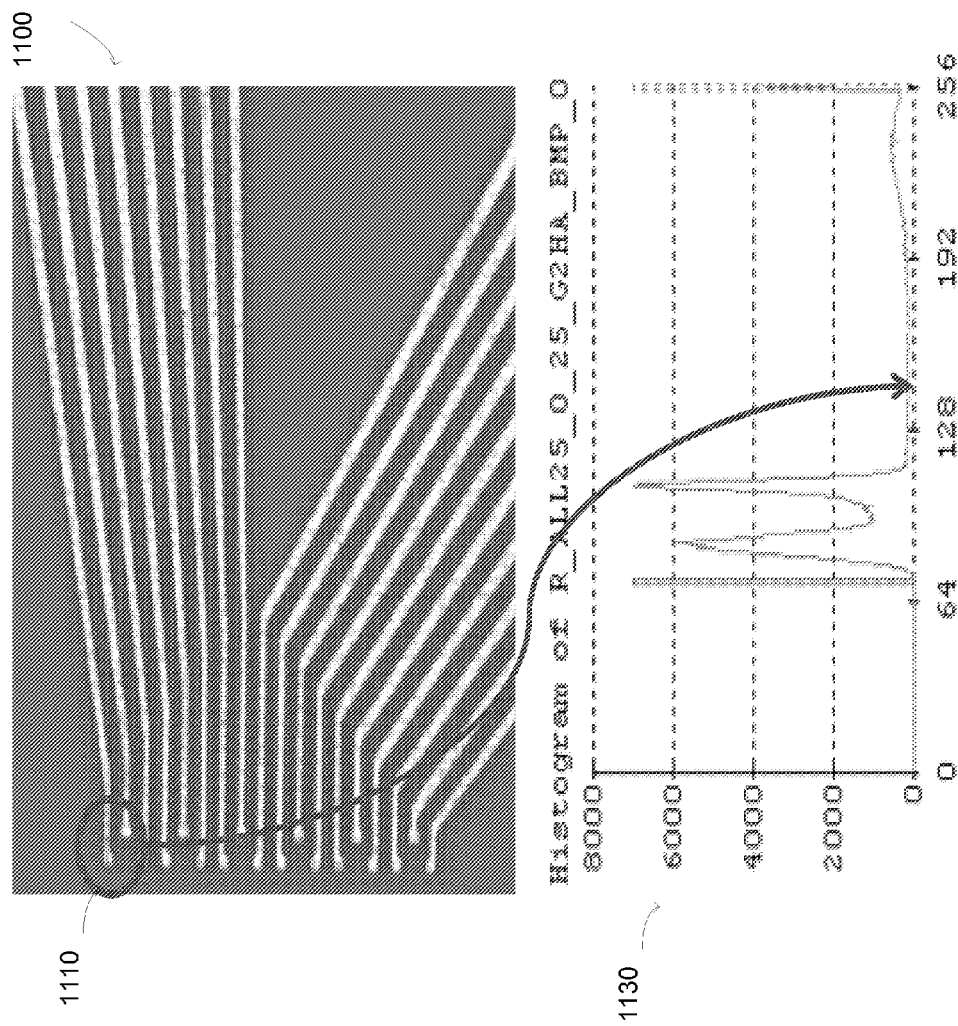
Figure 13:
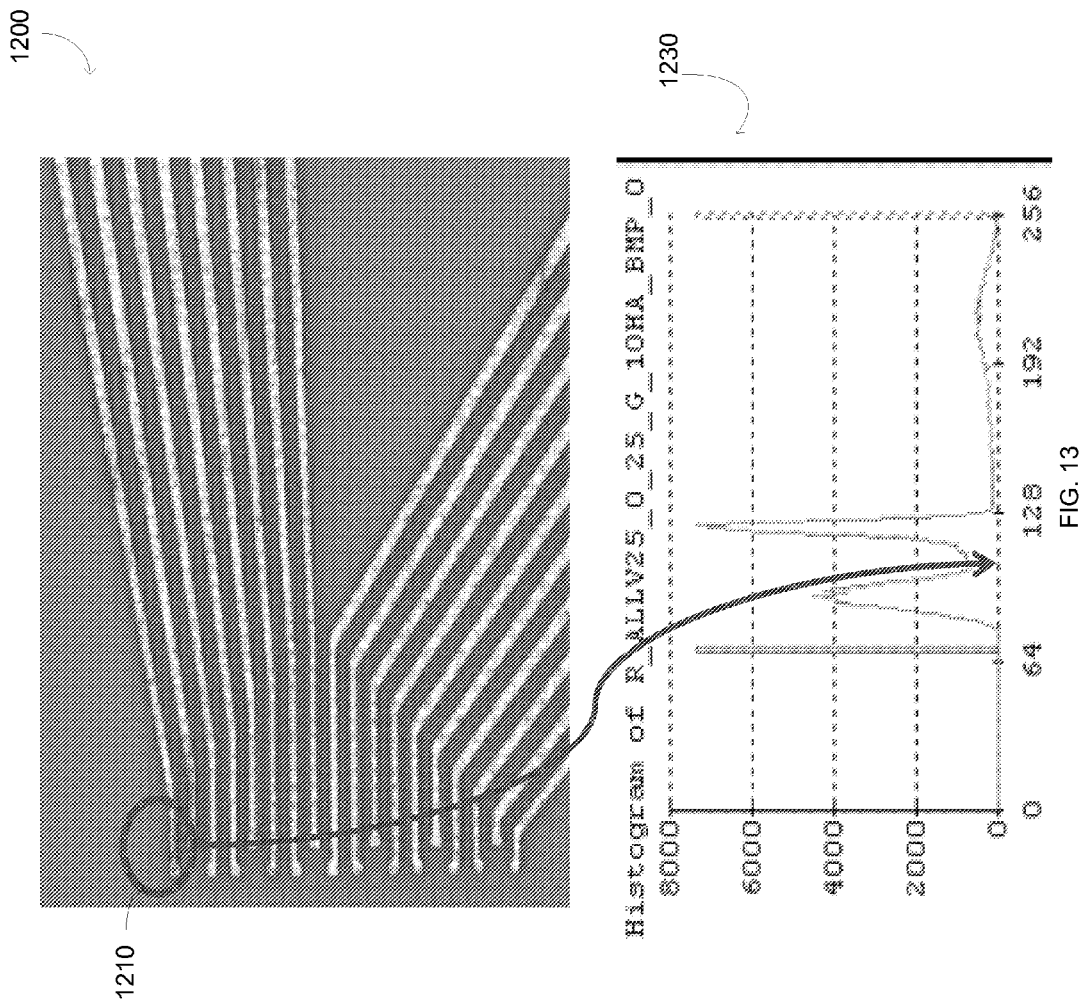
Figure 14:
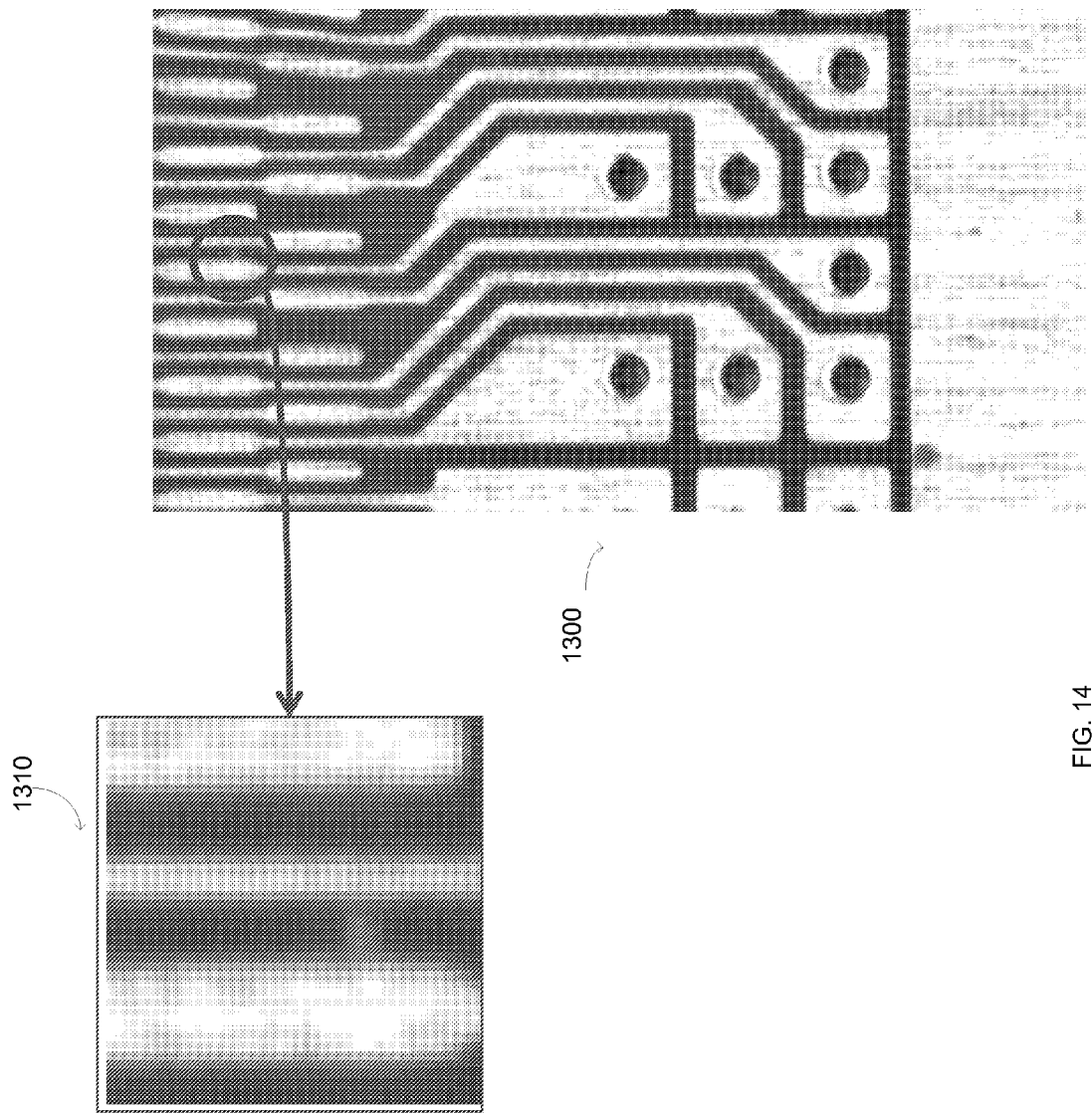
Figure 15:
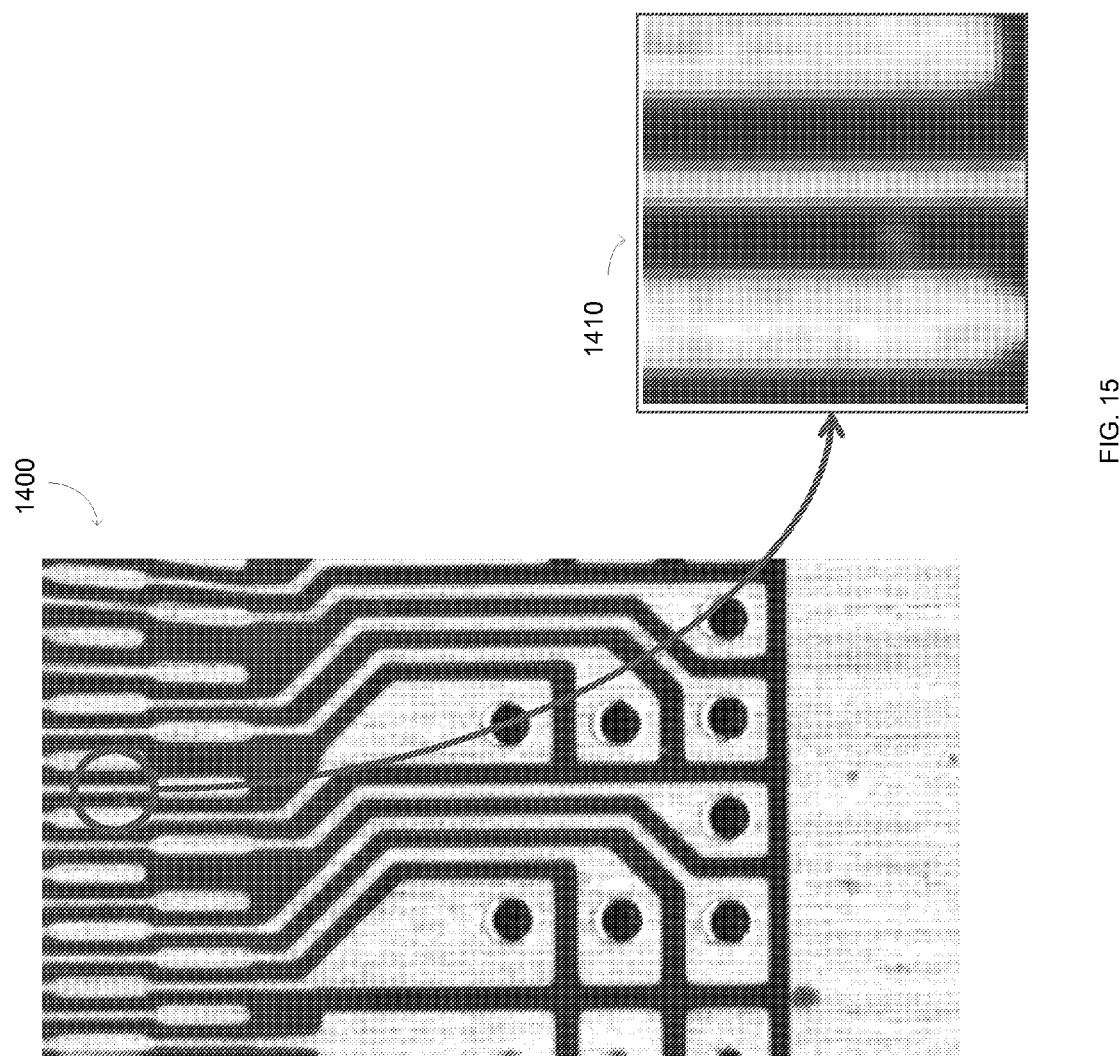
Figure 16:
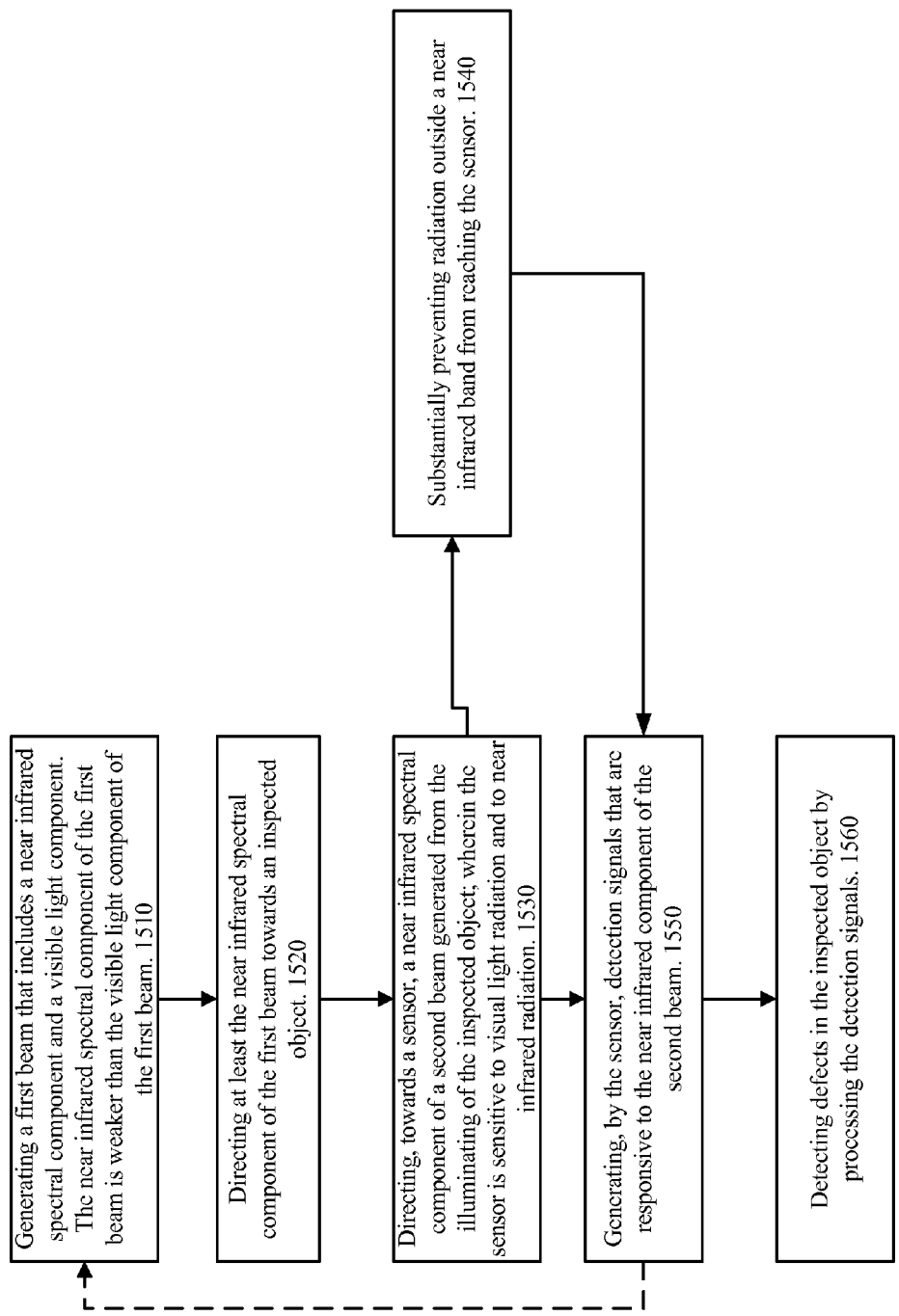
Figure 17:
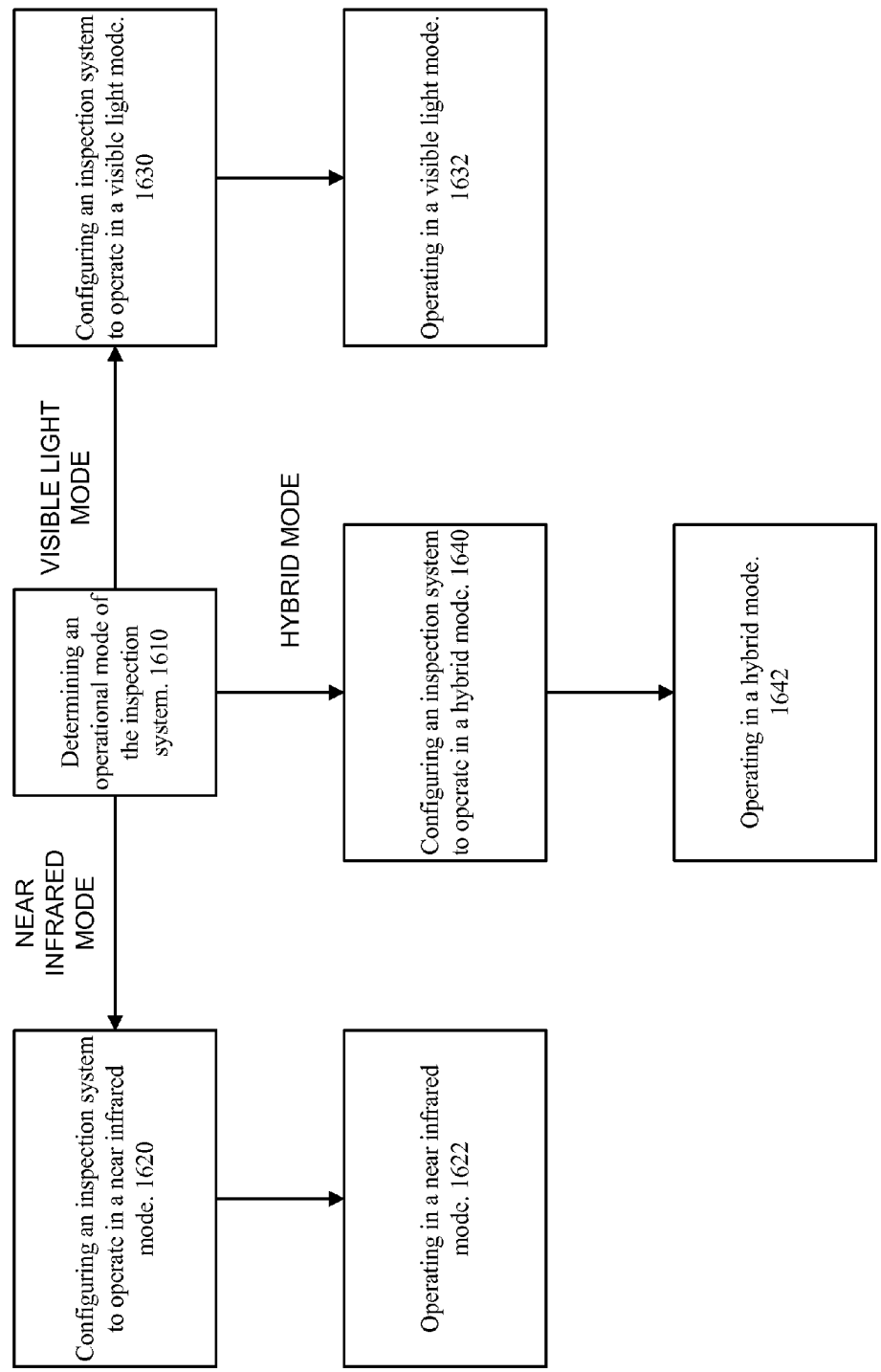

FIGS. 12 and 13 include images of narrow conductors placed on a Rodgers laminate material, obtained with different radiation bands and also illustrate histograms of portions of these images, according to an embodiment of the invention;

FIGS. 14 and 15 include images of a PCB that includes copper conductors placed on a laminate material and enlarged portions of these images, obtained in different wavelength ranges, according to an embodiment of the invention;

FIG. 16 illustrates a method for defect detection, according to an embodiment of the invention; and FIG. 17 illustrates a method for defect detection, according to another embodiment of the invention.

DETAILED DESCRIPTION OF THE PRESENT INVENTION

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

A method and an inspection system are provided. The inspection system may include a sensor that may operate in the visible light band and in the near infrared band and the method may include inspecting an inspected object at a near infrared band. The inspected object can include micro-metric and even nano-metric structures. The inspected object can be, for example, a semiconductor wafer, a printer circuit board (PCB), a wafer level package (WLP) wafer, one or more dice, one or more WLP dice, a lithographic mask, a MEMS (micro electrical mechanical system), and the like.

The wafer level package wafer (WLP) can be manufactured by attaching a several packaging layers on a semiconductor wafer and only after this attachment the product is diced to provide already packaged dices. It has been found that applying the suggested methods and systems on WLP wafers or WLP dice can reveal defects such as packaging related defects (misplacement of dice, glue or bonding materials misplacement, cracks in the package we well as dice defects).

Figure 1:
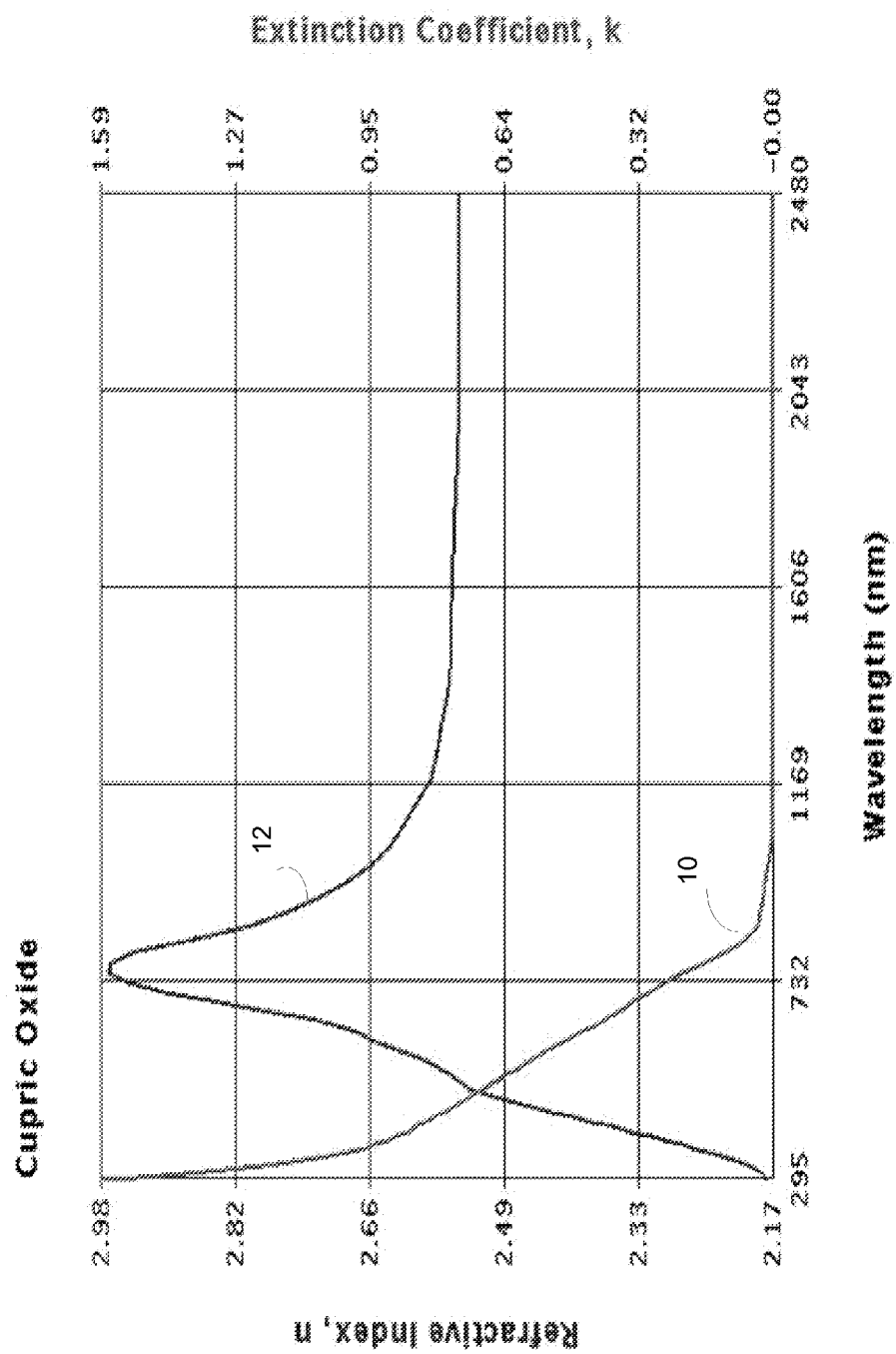
FIGS. 1 and 2 illustrate reactive index (n) and extinction coefficient (k) of Cupric Oxide and of Cuprous Oxide.
Figure 2:
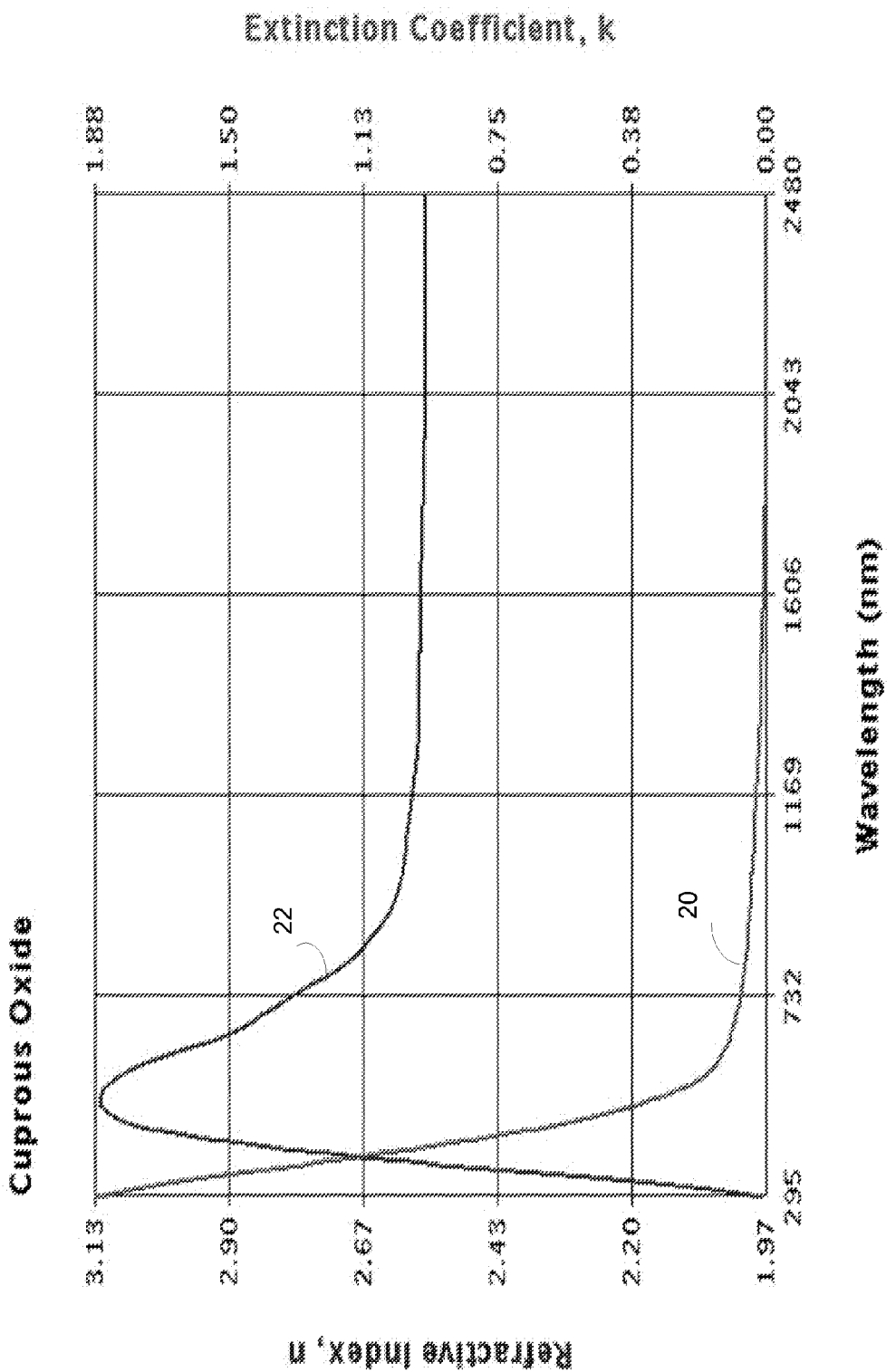

A desired upper boundary of the desired radiation band can be learnt from FIGS. 1 and 2. Radiation that has a wavelength below (or frequency above) the wavelength of the upper boundary should be blocked.

FIGS. 1 and 2 illustrate a reactive index (n) and an extinction coefficient (k) of Cupric Oxide and of Cuprous Oxide.

Curve 10 of FIG. 1 illustrates that the extinction coefficient of Cupric Oxide strongly decreases between the wavelengths of 295 nm and about 900 nm and slowly decreases between 900 nm and about 1000 nm. The extinction coefficient of Cupric Oxide is nearly zero above 1000 nm. Curve 12 of FIG. 1 illustrates that the refractive index of Cupric Oxide strongly increases between the wavelengths of 295 nm and 750 nm and then strongly decreases till about 1000 nm. The refractive index of Cupric Oxide slowly decreases till reaching a level of about 2.55 above 1400 nm.

Curve 20 of FIG. 2 illustrates that the extinction coefficient of Cuprous Oxide strongly decreases between the wavelengths of 295 nm and about 500 nm, decreases between 500 nm and about 700 nm and slowly decreases between 700 nm and 1606 nm. The extinction coefficient of Cuprous Oxide is nearly zero above 1300 nm. Curve 22 of FIG. 2 illustrates that the refractive index of Cuprous Oxide strongly increases between the wavelengths of 295 nm and 500 nm, decreases between 500 nm and about 850 nm and then slightly decreases till about 1200 nm. Between 1200 nm and 2480 nm the refractive index of Cuprous Oxide reaches a level of about 2.55.

Higher extinction coefficient values indicate that more light is absorbed and more dark pixels will appear in an image—thus causing more false defect calls.

Figure 3:
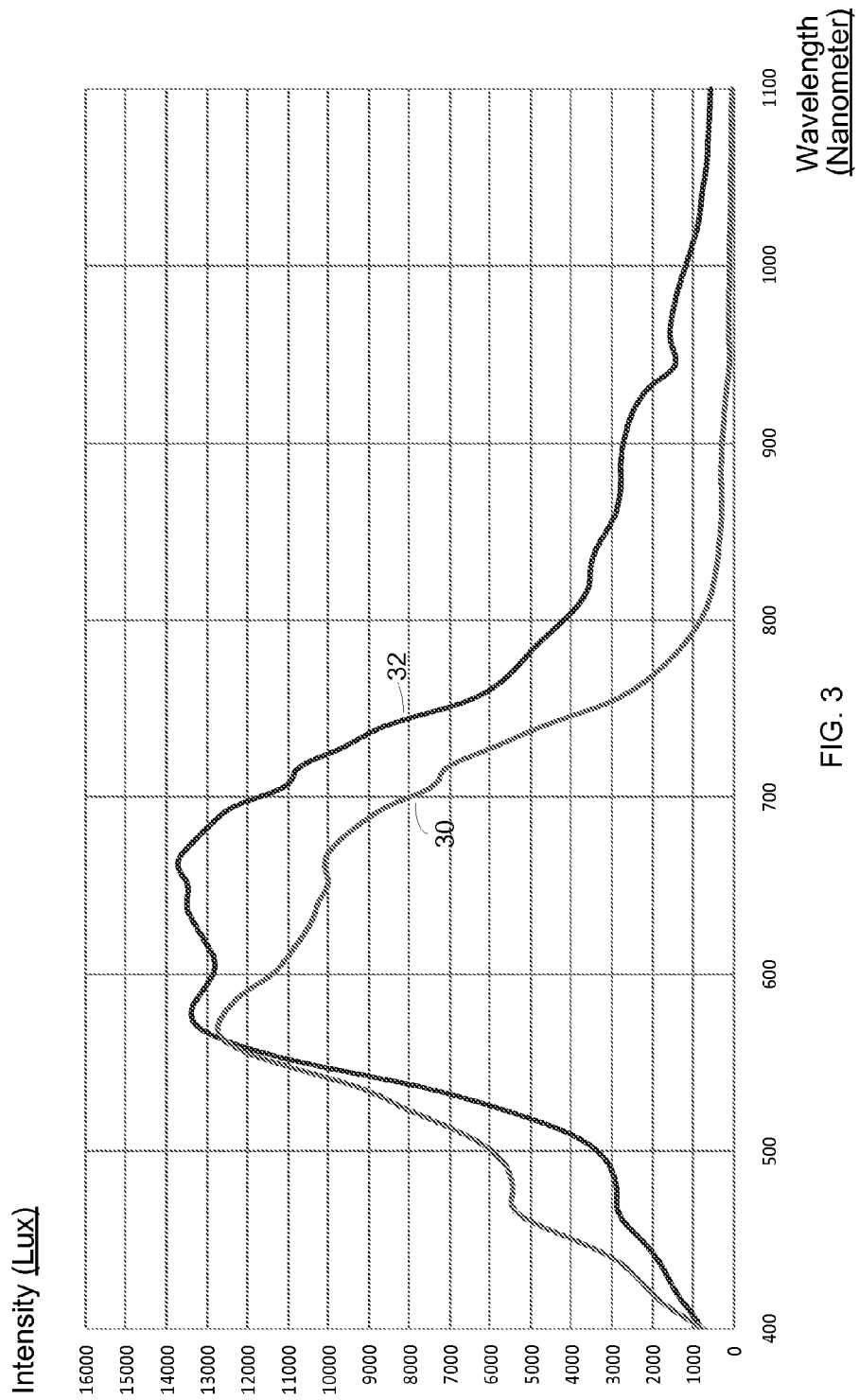
FIG. 3 illustrates a spectrum of two illumination sources according to an embodiment of the invention.
Figure 4:
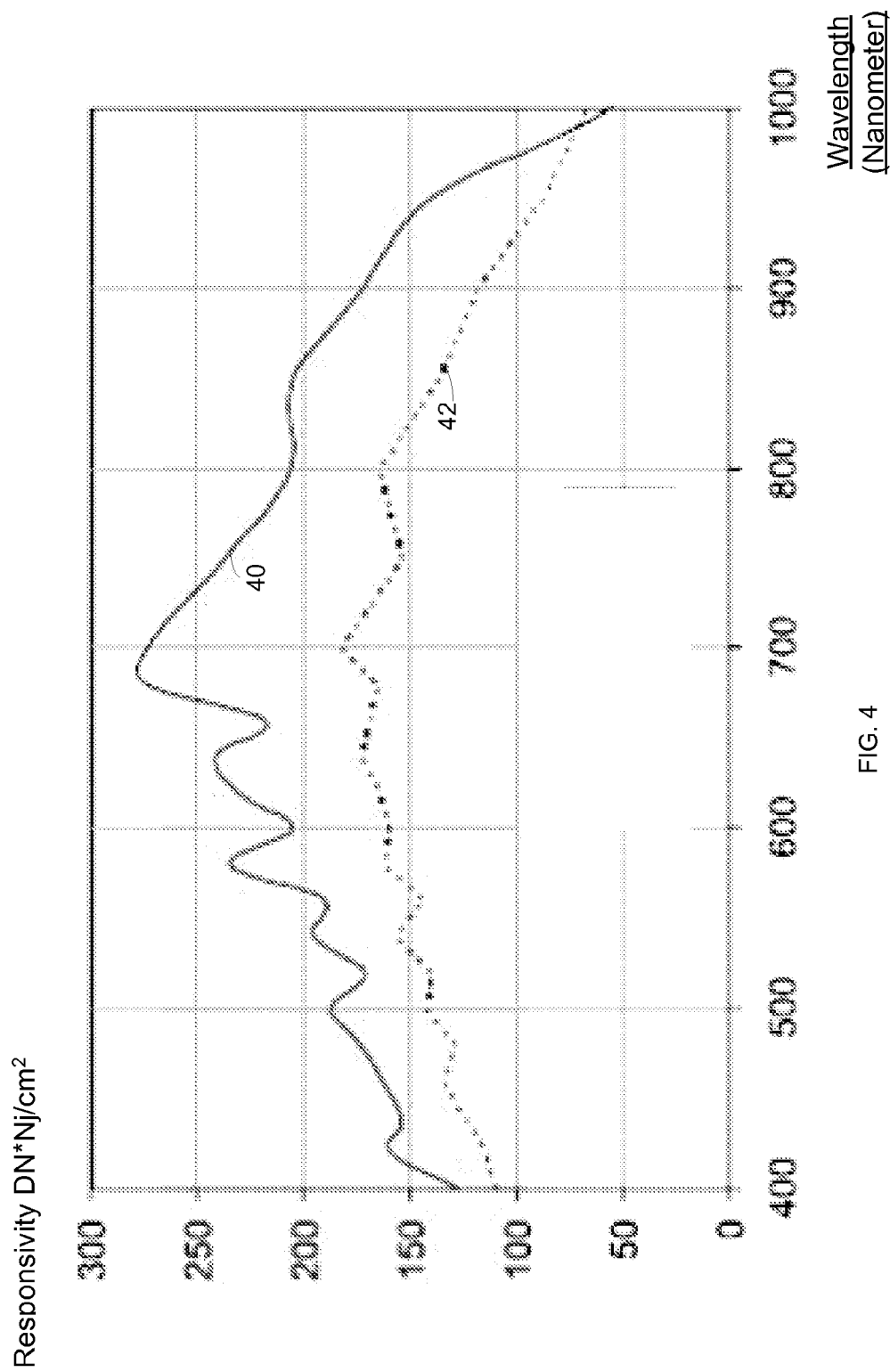
FIG. 4 illustrates a sensitivity of a Piranha 3 CCD camera of Dalsa Inc.

A desired lower boundary of the desired radiation band can be learnt from FIGS. 3 and 4. Radiation that has a wavelength above (or frequency below) the wavelength of the lower boundary should be blocked.

FIG. 3 illustrates a spectrum of two illumination sources. Curve 30 illustrates a spectrum of an illumination source that includes a L6409-G lamp with a Gold reflector and curve 32 illustrates a spectrum of an illumination source that includes an ELC-5h lamp with a Dichroic reflector.

Curve 30 illustrates that the combination of a L6409-G lamp and a Gold reflector emits radiation in the visible light and near infrared bands. Although the near infrared spectral components of the radiation is much weaker (visible light spectral components at wavelengths that range between 580 nm and 670 nm are about 13 times stronger than the near infrared spectral component at about 1000 nm). Nevertheless, these near infrared spectral components can still be used to illuminate an inspected object.

Curve 32 illustrates that an illumination source that includes an ELC-5h lamp with a Dichroic reflector less suitable then the combination of the L6409-G lamp and the Gold reflector for near infrared illumination as it omits nearly no radiation above 900 nm. Nevertheless, such an illumination source can be used when only a portion (for example 700 nm-800 nm) of the near infrared spectrum is used.

FIG. 4 illustrates a sensitivity of two CCD cameras Piranha 3 from Dalsa Inc., USA (Canada).

Curve 40 illustrates a sensitivity of a Piranha 3 CCD camera that has 5 micron pixels and curve 42 illustrates a sensitivity of a Piranha 3 CCD camera that has 7 micron pixels. In both cases the sensitivity strongly decreases above about 800 nm. At a wavelength of about 1000 nm the sensitivity of the 7 micron pixel camera is about 60 DN*Nj/cm$^2$ while the sensitivity of the 5 micron pixel is about 70 DN*Nj/cm$^2$. The peak sensitivity of the 5 micron camera is about 175 DN*Nj/cm$^2$ and the peak sensitivity of the 7 micron camera is about 275 DN*Nj/cm$^2$. Although not shown in this figure, the cut off frequency is about 1100 nm. This cut off frequency may determine the upper boundary of the desired radiation band.

According to an embodiment of the invention the desired radiation band is the near infrared band and especially wavelengths that range between about 700 nm and about 1100 nm. It is noted that the desired radiation band can also range between 710, 750, 800 and even 820 nm to about 900 nm, 1000 nm, 1100 nm or 1200 nm. Any portion of the 700 nm and about 1100 nm band can be used.

Radiation that is outside the near infrared band should be prevented from reaching the sensor, or at least substantially attenuated before reaching the sensor. Mid-infrared radiation and deep infrared radiation may cause strong image degradation if working with non-specialized imaging optics and sensor of an inspection system while visible light radiation introduces errors.

Figure 5:
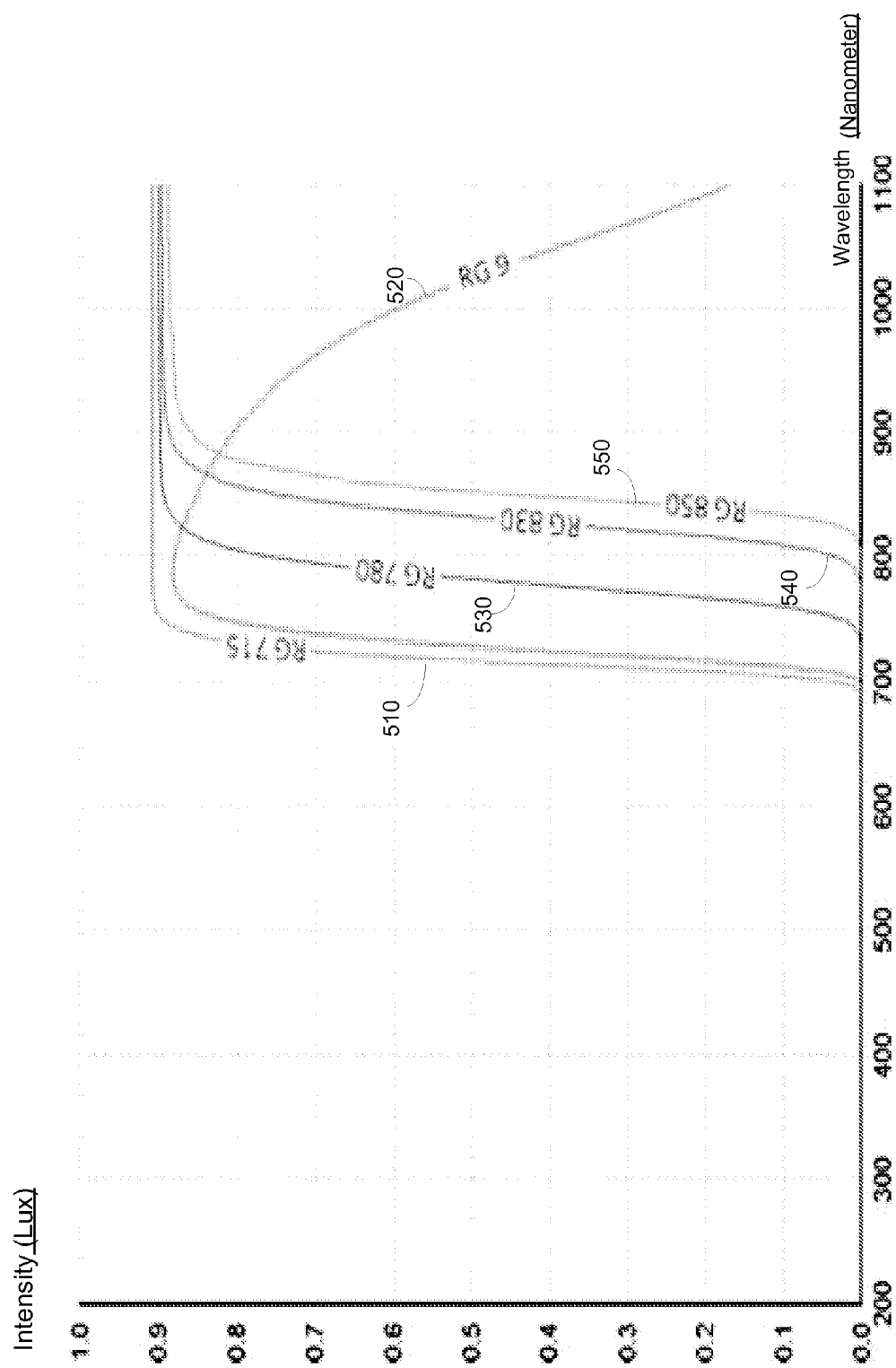
FIG. 5 illustrates transmission functions of various visible light blocking filters.

Various transmission functions of various visible light blocking filters are illustrated by curves 510, 520, 530, 540 and 550 of FIG. 5. These curve illustrate the transmission function of visible light blocking filters that filter radiation of wavelengths below 700 nm (RG715), below about 710 nm (RG9 filter), below about 750 nm (RG780), below about 800 nm (RG830) and below about 820 nm (RG 850).

Figure 6:
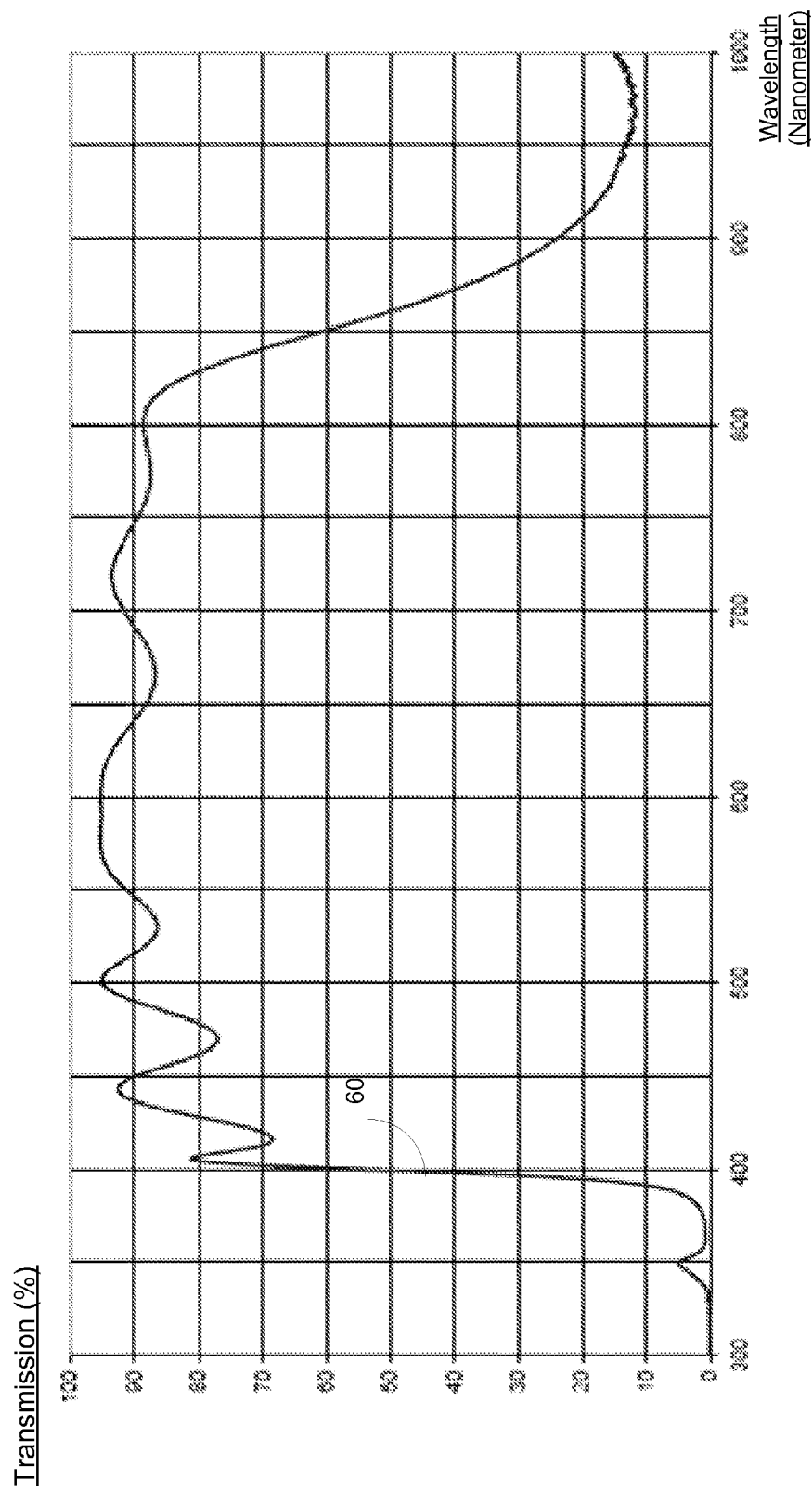
FIG. 6 illustrates a transmission function of an IR6 glass that functions as a hot mirror.

Curve 60 of FIG. 6 illustrates a transmission function of an IR6 glass that functions as a hot mirror—a filter that blocks mid infrared and far infrared radiation. Curve 60 illustrates a strong decrement in the transmission of radiation above 850 nm and especially illustrates a very low transmission factor at about 1000 nm.

According to an embodiment of the invention an inspection system may be provided. The inspection system may include a sensor that is sensitive to near infrared (NIR) radiation. This sensor can be also sensitive to visible light radiation and can be a low cost and even a standard visible light sensor. Such sensors are cheaper and even much cheaper than dedicated infrared sensors.

The inspection system may also include optics such as an imaging lens that may be a low cost and even a standard imaging lens that does not strongly degrade in NIR. The system may also include a light source that emits NIR radiation (possibly not restricted to NIR radiation) such as a low cost visible light source, and also includes a band pass filter. The band pass filter may include a hot mirror that transmits NIR radiation and rejects mid infrared radiation and far infrared radiation and has a cut-on filter that rejects visible light. The hot mirror can be an extended hot mirror and can be a standard and even a low cost hot mirror.

It is noted that the band-pass filter may include components other then the hot-mirror and cut-on filter.

The optics may include a beam splitter that receives a first beam from an illumination source, directs it towards the inspected object, receives a second beam from the inspected object and directs the second beam towards the sensor.

Figure 7:
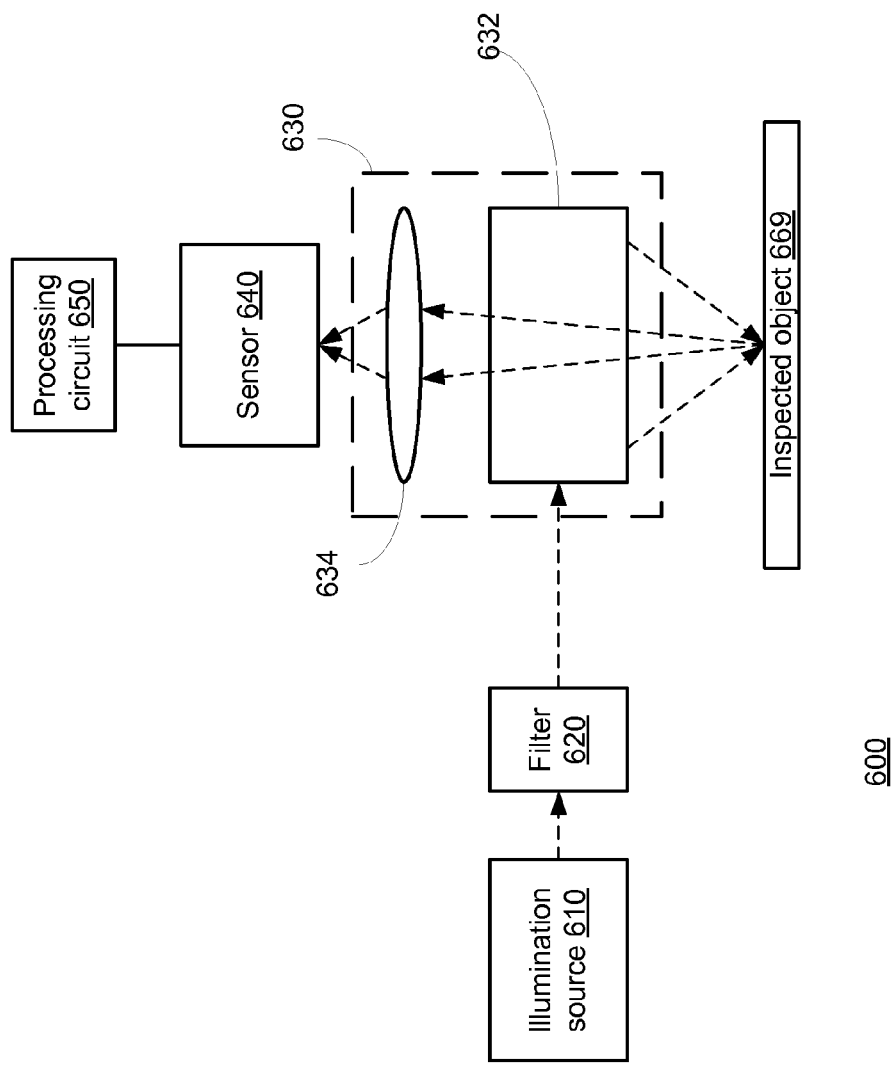
FIG. 7 illustrates an inspection system according to an embodiment of the invention.

FIG. 7 illustrates an inspection system 600 according to an embodiment of the invention.

The inspection system 600 may include an illumination source 610, a filter 620, optics 630, a sensor 640 and a processing circuit 650.

The illumination source 610 may be arranged to generate a first beam that includes a near infrared spectral component and a visible light component. The near infrared spectral component of the first beam may be weaker and can be much weaker than the visible light component of the first beam. This is not necessarily so and the near infrared spectral component of the first beam may be stronger than the visible light component of the first beam or equal to it.

The optics 630 is arranged to: (i) direct at least the near infrared spectral component of the first beam towards an inspected object; and (ii) direct, towards the sensor 640, a near infrared spectral component of a second beam generated from the illuminating of the inspected object 669.

The filter 620 is arranged to substantially prevent radiation outside a near infrared band from reaching the sensor 640. The substantially prevention of radiation may include allowing an insignificant amount of radiation outside the near infrared band to reach the sensor 640. The amount of radiation that is regarded as insignificant is determined in advance and can reflect an intensity of such radiation or an upper bound to the allowed error rate introduced by such radiation. Substantially preventing radiation can also be determined by the attenuation level of such radiation—for example an attenuation of 5 db, 10 db or more. FIGS. 5 and 6 provide non-limiting examples of transfer functions of a hot mirror and a cut-on filter that may form such a band pass filter.

The sensor 640 is sensitive to visual light radiation and to near infrared radiation. After the filtering operation of the filter 620, the sensor 640 is expected to provide detection signals that are responsive to the near infrared component of the second beam.

The processing circuit 650 is arranged to detect defects in the inspected object by processing these detection signals. The processing circuit 650 can include a memory module that stores the detection signals. Alternatively, the processing circuit 650 can be access a memory module that stores these detection signals.

It is further notes that the inspection system 600 can also include other components that are not shown for simplicity of explanation, such as (a) a mechanical stage that may support the inspected object 669 and may introduce movement between the inspected object 669 and either one of the optics 630, (b) a display, (c) a control panel, (d) an auto-focus circuit, and the like.

FIG. 7 illustrates optics 630 as including a beam splitter 632 and an imaging lens 634. FIG. 7 also illustrates filter 620 being located between the illumination source 610 and the beam splitter 632. It is noted that other configurations can be provided. For example, the filter 620 can be located between the beam splitter 632 (or the imaging lens 634) and the sensor 640. Yet for another example, the optics 630 may not include a beam splitter. Yet for another example, the optics 630 may include other components or additional optical components.

In the example illustrated in FIG. 7, the illumination source 610 generates a first light beam that includes a near infrared spectral component and a visible light component. It is noted that each of these spectral components can be monochromatic, narrow band or even wideband. A spectral component can include a single wavelength or a group of multiple wavelengths that can range between few nanometers end even hundred of nanometers. In the example set fourth in FIG. 3 the visible light spectral component ranges between 400 and 700 nm and the near infrared spectral component ranged between 700 nm and 1100 nm. Although not shown in FIG. 3, this first beam can include mid infrared and deep infrared spectral components.

The strength (intensity) of a spectral component can be represented by any predetermined function of the intensity of that spectral component. Non-limiting examples of such a predetermined function include a maximal intensity, an average intensity, a minimal intensity, a weighted average intensity and the like. Thus, a near infrared spectral component of a beam that is substantially weaker than a visible light spectral component of the beam means that the values of the predetermined function of the near infrared spectral component of a beam and of the predetermined function of the visible light spectral component indicate that the near infrared spectral component of the beam is substantially weaker than the visible light spectral component of the beam.

The filter 620 blocks spectral components other that the near infrared component of the first beam from reaching the beam splitter 632. The beam splitter 632 directs the near infrared spectral component of the first beam towards the inspected object 669 and also directs a near infrared component of a second beam (generated as a result of the illumination of the inspected object 669 by the near infrared spectral component of the first beam) towards imaging lens 634 and sensor 640.

If, for example, the filter 620 is located between the sensor 640 and the imaging lens 634 then the first light beam (including a spectral component outside the near infrared band) is directed by the beam splitter 632 towards the inspected object 669, a second light beam (including a spectral component outside the near infrared band) is directed by the beam splitter 632 towards the imaging lens 634 and is filtered before reaching the sensor 640.

Figure 8:
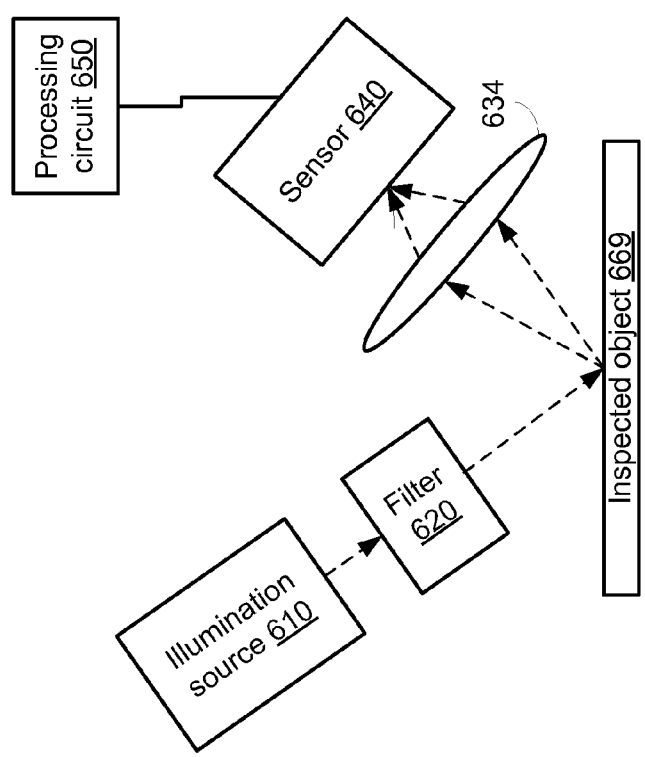
FIG. 8 illustrates an inspection system according to another embodiment of the invention.

FIG. 8 illustrates an inspection system 700 according to another embodiment of the invention.

Inspection system 700 differs from inspection system 600 by its optics 630—it does not include a beam splitter and both the illumination path (over which the first beam propagates towards the inspected object) and the collection path (over which the second beam propagates towards the sensor) are oriented in relation to an imaginary normal to the inspected object 669.

As illustrated in FIG. 8, the filter 620 follows the illumination source 610 and the near infrared component of the first beam impinges on the inspected object at an angle of about 60 degrees in relation to the normal to the inspected object 669. The near infrared component of the second beam is collected by the imaging lens 634 at a collection angle of about −60 degrees in relation to the imaginary normal.

Although the collection path and the illumination path of inspection system 700 are symmetrical about the imaginary normal this is not necessarily so and the collection angle can differ from the illumination angle.

The configuration of FIG. 8 is beneficial in the sense that the imaging lens 634 collects reflected radiation (of significant intensity) and that the illumination substantially differs from normal illumination—thus reducing the affect of oxidation on the detected signals. Thus, oxidized metals will appear as non-oxidized metals. Even oxidized defects can be better images as the detection signals are substantially indifferent to the oxidation of the oxidized defects.

In either one of inspection systems 600 and 700 the near infrared spectral component of the first beam may be substantially weaker than the at least one visible light component of the first light beam.

In either one of inspection systems 600 and 700 the sensor 620 may be arranged to generate detection signals that are substantially indifferent to different levels of oxidation of the metal elements of the inspected object.

In either one of inspection systems 600 and 700 the near infrared spectral component of the first beam is at least ten times weaker than the visible light component of the first beam.

Figure 9:
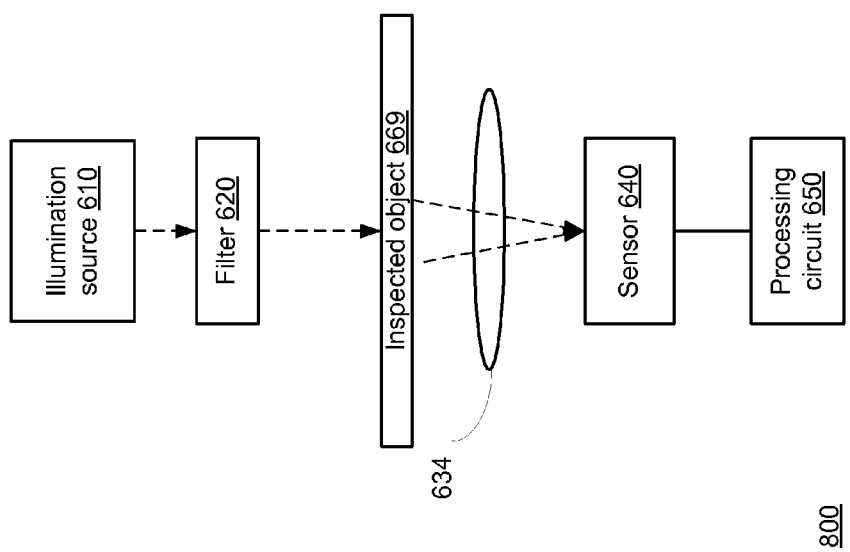
FIG. 9 illustrates an inspection system according to a further embodiment of the invention.

FIG. 9 illustrates an inspection system 800 according to another embodiment of the invention.

Inspection system 800 differs from inspection system 600 by its optics 630 and by the location of sensor 640. Inspection system 800 operates in a transmissive mode and does not include a beam splitter. Sensor 640 and illumination source 610 are positioned at opposite sides of the inspected object 669. For example, illumination source 610 can be positioned above the inspected object 669 while the sensor 640 can be positioned below the inspected object 669.

In FIG. 8, both the illumination path and the collection path are normal to the inspected object 669 but this is not necessarily so and at least one path can be oriented to the normal.

As illustrated in FIG. 9, the filter 620 follows the illumination source 610 and the near infrared component of the first beam impinges on the inspected object 669 at an angle of about 60 degrees. The second beam includes a near infrared component that passes through the inspected object 669 and is collected by the imaging lens 634 and then directed towards sensor 640.

The inspected object 669 may include silicon and metal structures (it may be a silicone wafer) and the sensor 640 may be located to sense a near infrared spectral component of the second beam that passes through the inspected object 669. Silicone is virtually transparent to near infrared radiation and imaging system 800 can provide information about metal elements of such an inspected object 669.

Either one of inspection systems 600, 700 and 800 can operate in a near infrared mode in which the sensor 640 detects near infra red radiation. Additionally or alternatively, either one of inspection systems 600, 700 and 800 can operate in a visual light mode in which the sensor 640 detects visible light. Additionally or alternatively, either one of inspection systems 600, 700 and 800 can operate in a hybrid mode in which the sensor 640 detects both visible light and near infrared radiation.

The switching between modes may include re-configuring or switching the filter 620. The filter 620 can include multiple filtering components that can be mechanically replaced by each other to facilitate the different modes of operation. The filters can be mechanically moved to be in the path of either the first or second beams or be away from such a path. For example, band pass filter the blocks visible light radiation and passes near infrared radiation can be replaced by a filter that passes visible light radiation or by a filter that blocks near infrared radiation and passes visible light radiation. The filters can be located on a torrent that can be rotated about its center to expose a beam to different filters.

Inspection systems 600 and 700 can be used for various purposes. For example, these inspection systems can be used to inspect objects that have metal elements (such as conductors or pads) that may be oxidized, and additionally or alternatively, can be used to inspect objects that include metal elements and laminate or dielectric elements. Non-limiting examples include PCB that may include a White Teflon™ or Alumina substrate, and the like.

Such inspection systems can be used to sense near infrared radiation within a near infrared band that ranges between 820 nm to 1100 nm. Such inspection systems can, for example, reduce Copper Oxide false errors (false positives), can increase the global contrast of Oxides in various layers of the PCB (or other inspected objects, e.g. other electrical circuits) such as inner layers, outer layers and White Teflon™ layers, increases the local contrast of small features with and without Oxides.

According to an embodiment of the invention the filter may pass only a portion of the near infrared range. For example, passing near infrared spectral components of higher wavelengths can decrease the difference between pixels obtained by illuminating Copper and Copper Oxides.

The illumination angle of either one of the inspection systems 600, 700 and 800 can be altered or be arranged to differ from normal illumination. It has been found that greater deviations of the illumination angle from normal illumination can reduce the unwanted effect of oxidations.

Either one of inspection systems 600, 700 and 800 can use longer wavelengths (in the near infrared band) such as to increase the contrast between Copper and Glass-Epoxy (e.g. Inner, Outer Layers) and between Copper and White Teflon™ laminate.

Figure 10:
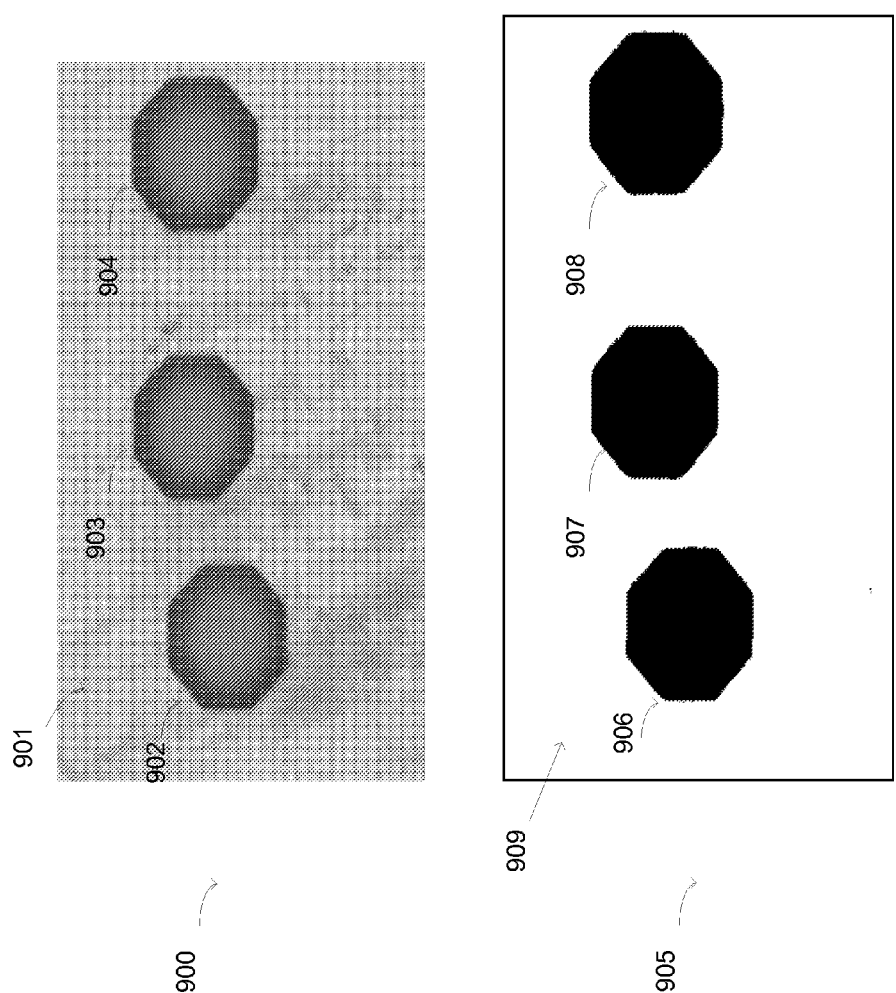

FIG. 10 illustrates an image 900 and a binary image 905 of an area of an inspected object acquired with a near infrared radiation band of 830-1100 nm, according to an embodiment of the invention.

Image 900 includes images 902-904 of three octagons of a first material, these images are surrounded by an image 901 of another material that forms a background to the octagons. These first and second materials can be laminate and copper. There is a clear contrast between the images 902-904 of the three octagons and the image 901 of the background. All pixels or almost all pixels of the images 902-904 of the three octagons are darker than almost all (or all) pixels of the image of the background—thus, image 900 can be binarized to provide binary image 906 that includes three black images 907-909 of the octagons, these three images are surrounded by a white image 906 that represents the background.

FIG. 11 illustrates an image 910 and a binary image 915 of the same area of the inspected object as illustrated in FIG. 10 but acquired with a radiation band of 650-900 nm.

Image 920 includes images 912-914 of three octagons of the first material, these images are surrounded by an image 911 of a background made of another material. Many pixels of the images 912-914 of the three octagons are darker than many pixels of the image 911 of the background. Many pixels of the images 912-914 of the three octagons are brighter than many pixels of the image 911 of the background. Accordingly—image 910 cannot be binarized in a manner that provides an exact representation of the octagons and of the background.

Binarized image 919 includes images 916-918 of three black octagon-shaped rings having a white center and a background image 919 that includes a majority of white pixels but many black pixels 920. The black pixels 920 and the white centers can cause false positives.

FIGS. 12 and 13 include images 1100 and 1200 of narrow conductors placed on a White Teflon™ laminate material, image 1100 obtained with radiation within a near infrared band of 830-1100 nm, and image 1200 obtained with radiation that ranges between 650-900 nm. These figures also illustrate histograms 1120 and 1220 of portions 1110 and 1210 of images 1100 and 1200.

The contrast between the narrow conductors and the White Teflon™ laminate material in image 1100 is sharper than the corresponding contrast in image 1200. The narrow conductors of image 1100 are brighter and are more homogenous than the corresponding narrow conductors of image 1200.

Portions 1110 and 1210 include pixels from an area that includes the ends of two narrow conductors and a surrounding dielectric material. The histogram 1120 of portion 1110 includes a region that includes most pixels and has two major peaks and the gray level value of Oxidized Copper is positioned outside this region. The histogram 1220 of portion 1210 includes a region that includes most pixels and has two major peaks and the gray level value of Oxidized Copper is positioned within this region—between the two peaks.

FIGS. 14 and 15 include images 1300 and 1400 a PCB that include copper conductors placed on a laminate material, image 1300 obtained with radiation within a near infrared band of 830-1100 nm, and image 1400 obtained with radiation that ranges between 650-900 nm. These figures also illustrate enlarged portions 1310 and 1410 of images 1300 and 1400.

Fine defects (very bright pixels) can be better viewed in enlarged portion 1310 of image 1300. This enlarged portion 1310 includes more information about the shape of these fine defects then enlarged portion 1410 of image 1400.

According to an embodiment of the invention, an imaging (and/or inspection) method is disclosed, the method includes directing near-infrared illumination onto an object (e.g. an electrical circuit, a PCB board), and imaging reflected near infrared illumination which is reflected from the object by a sensor that is adapted to image at least in a portion of the near infrared spectrum. According to an embodiment of the invention, the imaging includes imaging at least a portion of the reflected illumination which is reflected from a copper part of the object and/or imaging at least a portion of the reflected illumination which is reflected from a copper compound (e.g. cupric oxide, cuprous oxide) part of the object.

According to an embodiment of the invention, the illuminating includes blocking illumination in frequencies other than near infrared. It should be noted that preventing infrared illumination (e.g. mid infrared, far infrared), by way of example, prevents image quality degradation and even unnecessary heating of the object. It is noted that various embodiments of the method may include various embodiments discussed in relation to the aforementioned systems.

FIG. 16 illustrates method 1500 for defect detection, according to an embodiment of the invention.

Method 1500 includes stage 1510 of generating a first beam that includes a near infrared spectral component and a visible light component. The near infrared spectral component of the first beam may be weaker than the visible light component of the first beam.

Stage 1510 may include generating a first light beam wherein the near infrared spectral component of the first beam may be substantially weaker than the at least one visible light component of the first light beam.

The near infrared band may range between a wavelength of about 700 nanometers and a wavelength of about 1100 nanometers. The near infrared spectral component of the first beam may be at least ten times weaker than the visible light component of the first beam.

Stage 1510 is followed by stage 1520 of directing at least the near infrared spectral component of the first beam towards an inspected object.

Stage 1520 may include directing the first beam at an angle that is normal to the inspected object. Alternatively, stage 1520 may include directing the first beam that is oriented in relation to an imaginary normal to the inspected object by at least twenty degrees or by at least sixty degrees.

Stage 1520 is followed by stage 1530 of directing, towards a sensor, a near infrared spectral component of a second beam generated from the illuminating of the inspected object; wherein the sensor is sensitive to visual light radiation and to near infrared radiation.

FIG. 16 illustrates stage 1540 as being parallel to stage 1530. This is not necessarily so. For example, stage 1540 can preceded either one of stages 1520 and 1530. Stage 1540 includes substantially preventing radiation outside a near infrared band from reaching the sensor.

Stage 1530 and optionally stage 1540 are followed by stage 1550 of generating, by the sensor, detection signals that are responsive to the near infrared component of the second beam.

Stage 1550 is followed by stage 1560 of detecting defects in the inspected object by processing the detection signals.

It is noted that the first beam can illuminate a small area or a large area of the inspected object. This area can have different shapes. In order to illuminate multiple areas of the inspected object, method 500 may include illuminating one area after the other and obtaining detection signals representing multiple areas. This is represented by a dashed arrow from box 1550 to box 1510. This repetition may include using pulsed illumination, continuous illumination, optically scanning the inspected object, mechanically moving the inspected object, mechanically moving the optics, and the like.

Method 500 can be applied in a reflective mode or in a transmissive mode. Referring to the examples set fourth in previous figures, method 500 can be executed by either one of inspection systems 600, 700 and 800.

Method 500 can be applied to inspect an inspected object that includes silicon and metal structures, and stage 1550 may include generating, by the sensor, detection signals that are responsive the near infrared spectral component of the second beam that passes through the inspected object.

Method 500 can be applied to inspect metal elements of an inspected object and stage 1550 may include generating, by the sensor, detection signals that are substantially indifferent to different levels of oxidation of the metal elements of the inspected object.

The sensor may be a visible light sensor that is also arranged to sense near infra red radiation.

FIG. 17 illustrates method 1600 for defect detection, according to an embodiment of the invention.

Method 1600 differs from method 1500 by including multiple operational modes—a near infrared mode in which method 1500 is executed, a visible light mode in which visible light images are acquired and processed, and a hybrid mode in which images that are sensitive to both visible light and near infrared radiation are acquired. This hybrid mode can be implemented by not blocking visible light and near infrared radiation.

Method 1600 includes stages 1610, 1620, 1622, 1630, 1632, 1640 and 1620.

Stage 1610 includes determining an operational mode of the inspection system. The determination is made by an operator or can be a part of an inspection recipe. The determination may be triggered by a completion of a portion of an inspection recipe, can be triggered by events such as a detection of defects, an end of an inspection of a predefined area of an inspected object and the like. For example, more critical areas (to the functionality of the inspected object) or more error prone areas can be inspected by two different modes.

The operational mode can include a near infrared mode and at least one mode out of a visible light mode and hybrid mode. FIG. 17 illustrates all three modes.

If stage 1610 includes determining to operate in a near infrared mode then stage 1610 is followed by stage 1620 of configuring an inspection system to operate in a near infrared mode. Stage 1620 is followed by stage 1622 of operating in a near infrared mode. The configuration can include altering a characteristic of an illumination unit, of a filter or of optics. The configuration can include replacing a component, adjusting a component and the like. For example an inspection system can include a bank of filters and the configuration can include selecting one filter of the bank.

Stage 1622 can include at least some of the stages of method 1500- and can include all the stages of method 1500. For example, stage 1622 may include: (i) generating a first beam that includes a near infrared spectral component and a visible light component; (ii) directing at least the near infrared spectral component of the first beam towards an inspected object; (iii) directing, towards a sensor, a near infrared spectral component of a second beam generated from the illuminating of the inspected object; wherein the sensor is sensitive to visual light radiation and to near infrared radiation; (iv) substantially preventing radiation outside a near infrared band from reaching the sensor; (v) generating, by the sensor, detection signals that are responsive to the near infrared component of the second beam; and (vi) detecting defects in the inspected object by processing the detection signals.

If stage 1610 includes determining to operate in a visible light mode then stage 1610 is followed by stage 1630 of configuring an inspection system to operate in a visible light mode. The configuration can include altering a characteristic of an illumination unit, of a filter or of optics. The configuration can include replacing a component, adjusting a component and the like. For example an inspection system can include a bank of filters and the configuration can include selecting one filter of the bank.

Stage 1630 is followed by stage 1632 of operating in a visible light mode. Stage 1632 may include: (i) generating a first beam that includes a near infrared spectral component and a visible light component; (ii) directing at least the visible light component of the first beam towards an inspected object; (iii) directing, towards a sensor, the visible light component of a second beam generated from the illuminating of the inspected object; wherein the sensor is sensitive to visual light radiation and to near infrared radiation; (iv) substantially preventing radiation outside the visible light band from reaching the sensor; (v) generating, by the sensor, detection signals that are responsive to the visible light component of the second beam; and (vi) detecting defects in the inspected object by processing the detection signals.

If stage 1610 includes determining to operate in a hybrid mode then stage 1610 is followed by stage 1640 of configuring an inspection system to operate in a hybrid mode. The configuration can include altering a characteristic of an illumination unit, of a filter or of optics. The configuration can include replacing a component, adjusting a component and the like. For example an inspection system can include a bank of filters and the configuration can include selecting one filter of the bank.

Stage 1640 is followed by stage 1642 of operating in a hybrid mode. Stage 1642 may include: (i) generating a first beam that includes a near infrared spectral component and a visible light component; (ii) directing the near infrared spectral component and the visible light component of the first beam towards an inspected object; (iii) directing, towards a sensor, a near infrared spectral component and a visible light component of a second beam generated from the illuminating of the inspected object; wherein the sensor is sensitive to visual light radiation and to near infrared radiation; (iv) substantially preventing radiation outside a near infrared band and outside the visible light band from reaching the sensor; (v) generating, by the sensor, detection signals that are responsive to the near infrared component and to the visible light component of the second beam; and (vi) detecting defects in the inspected object by processing the detection signals.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for defect detection, the method comprises:
   generating a first beam that comprises a near infrared spectral component and a visible light component;
   directing at least the near infrared spectral component of the first beam towards an inspected object;
   directing, towards a sensor, a near infrared spectral component of a second beam generated from the illuminating of the inspected object; wherein the sensor is sensitive to visual light radiation and to near infrared radiation;
   generating, by the sensor, detection signals that are responsive to the near infrared component of the second beam; and
   detecting defects in the inspected object by processing the detection signals.

2. The method according to claim 1, further comprising substantially preventing radiation outside a near infrared band from reaching the sensor.

3. The method according to claim 1, wherein the inspected object comprises at least one out of silicon and metal structures, and wherein sensor is located to sense a near infrared spectral component of the second beam that passes through the inspected object.

4. The method according to claim 1, comprising directing at least the near infrared spectral component of the first beam towards metal elements of the inspected object; and generating, by the sensor, detection signals that are substantially indifferent to different levels of oxidation of the metal elements of the inspected object.

5. The method according to claim 1, wherein the sensor is a visible light sensor that is also arranged to sense near infra red radiation.

6. The method according to claim 1, comprising:
   substantially preventing radiation outside a near infrared band from reaching the sensor and generating, by the sensor, detection signals that are responsive to the near infrared component of the second beam, when an inspection system that comprises the sensor operates in a near infra red mode; and substantially preventing radiation outside a visible light band from reaching the sensor and generating, by the sensor, detection signals that are responsive to a visible light component of the second beam, when the inspection system operates in a visual light mode.

7. The method according to claim 1, wherein the near infrared band ranges between a wavelength of about 700 nanometers and a wavelength of about 1100 nanometers.

8. The method according to claim 1, wherein the illuminating comprises directing the first beam at an angle that is oriented in relation to an imaginary normal to the inspected object by at least twenty degrees.

9. The method according to claim 1, wherein the illuminating comprises directing the first beam at an angle that is oriented in relation to an imaginary normal to the inspected object by about sixty degrees.

10. An inspection system, comprising:
    an illumination source arranged to generate a first beam that comprises a near infrared spectral component and a visible light component;
    optics arranged to:
    direct at least the near infrared spectral component of the first beam towards an inspected object;
    direct, towards a sensor, a near infrared spectral component of a second beam generated from the illuminating of the inspected object; wherein the sensor is sensitive to visual light radiation and to near infrared radiation;
    wherein the sensor is arranged to detect signals that are responsive to the near infrared component of the second beam; and
    a processing circuit arranged to detect defects in the inspected object by processing the detection signals.

11. The inspection system according to claim 10, further comprising a filter for substantially preventing radiation outside a near infrared band from reaching the sensor.

12. The inspection system according to claim 10, wherein the inspected object comprises at least one out of silicon and metal structures, and wherein sensor is located to sense a near infrared spectral component of the second beam that passes through the inspected object.

13. The inspection system according to claim 10, wherein the optics is arranged to direct at least the near infrared spectral component of the first beam towards metal elements of the inspected object; and wherein the sensor is arranged to generate detection signals that are substantially indifferent to different levels of oxidation of the metal elements of the inspected object.

14. The inspection system according to claim 10, wherein the sensor is a visible light sensor that is also arranged to sense near infra red radiation.

15. The inspection system according to claim 10, wherein the filter is arranged to substantially prevent radiation outside a near infrared band from reaching the sensor and the sensor is arranged to generate detection signals that are responsive to the near infrared component of the second beam, when the inspection system operates in a near infra red mode; and wherein the filter is further arranged to substantially prevent radiation outside a visible light band from reaching the sensor and the sensor is further arranged to generate detection signals that are responsive to a visible light component of the second beam, when the inspection system operates in a visual light mode.

16. The inspection system according to claim 10, wherein the near infrared band ranges between a wavelength of about 700 nanometers and a wavelength of about 1100 nanometers.

17. The inspection system according to claim 10, wherein the optics are arranged to direct the first beam at an angle that is oriented in relation to an imaginary normal to the inspected object by at least twenty degrees.

18. The inspection system according to claim 10, wherein the optics is arranged to direct the first beam at an angle that is oriented in relation to an imaginary normal to the inspected object by about sixty degrees.

* * * * *